US010542947B2

(12) United States Patent
Kojima et al.

(10) Patent No.: US 10,542,947 B2
(45) Date of Patent: Jan. 28, 2020

(54) PHOTON-COUNTING CT APPARATUS

(71) Applicant: Hitachi, Ltd., Chiyoda-ku, Tokyo (JP)

(72) Inventors: Shinichi Kojima, Tokyo (JP); Yasutaka Konno, Tokyo (JP); Fumito Watanabe, Tokyo (JP); Isao Takahashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/071,810

(22) PCT Filed: Nov. 17, 2016

(86) PCT No.: PCT/JP2016/084099
§ 371 (c)(1),
(2) Date: Jul. 20, 2018

(87) PCT Pub. No.: WO2017/126208
PCT Pub. Date: Jul. 27, 2017

(65) Prior Publication Data
US 2019/0021685 A1 Jan. 24, 2019

(30) Foreign Application Priority Data
Jan. 22, 2016 (JP) ................................. 2016-010455

(51) Int. Cl.
A61B 6/00 (2006.01)
A61B 6/03 (2006.01)
G06T 11/00 (2006.01)

(52) U.S. Cl.
CPC ............ A61B 6/4241 (2013.01); A61B 6/032 (2013.01); A61B 6/585 (2013.01); G06T 11/005 (2013.01); A61B 6/4035 (2013.01)

(58) Field of Classification Search
CPC .......... A61B 6/03; A61B 6/032; A61B 6/4035; A61B 6/4241; A61B 6/585; G06T 11/005
See application file for complete search history.

(56) References Cited

U.S. PATENT DOCUMENTS 5,991,358 A 11/1999 Dolazza et al.
6,256,364 B1 7/2001 Toth et al.
(Continued)

FOREIGN PATENT DOCUMENTS

JP 7-384 A 1/1995
JP 8-24251 A 1/1996
(Continued)

OTHER PUBLICATIONS

Japanese-language Office Action issued in counterpart Japanese Application No. 2016-010455 dated Feb. 26, 2019 with English translation (six (6) pages).
(Continued)

Primary Examiner — Dani Fox
(74) Attorney, Agent, or Firm — Crowell & Moring LLP

(57) ABSTRACT

The present invention is directed to make a photon-counting CT apparatus capable of more accurate data acquisition. Such apparatus is provided with a reference detection unit and a time measuring instrument to measure temporal fluctuations in a rotational direction of an X-ray irradiation unit. The apparatus corrects temporal fluctuations in the rotational direction involved in data measured by the reference detection unit, using time measurement data which is output by the time measuring instrument. Using corrected measurement data measured by the reference detection unit, the apparatus makes corrections of fluctuations pertaining to the X-ray tube of the X-ray irradiation unit and pile-up. Data corrections with high accuracy are thus enabled.

14 Claims, 13 Drawing Sheets

(56) References Cited

U.S. PATENT DOCUMENTS

| | | | |
|---|---|---|---|
| 2013/0287165 A1* | 10/2013 | Sharpless | A61B 6/032 378/19 |
| 2015/0160355 A1 | 7/2015 | Wang et al. | |
| 2015/0198725 A1 | 7/2015 | Tamura et al. | |
| 2015/0287221 A1 | 10/2015 | Takayama et al. | |
| 2016/0022243 A1* | 1/2016 | Nakai | A61B 6/483 378/5 |

FOREIGN PATENT DOCUMENTS

| | | | |
|---|---|---|---|
| JP | 2002-530140 A | 9/2002 |
| JP | 2014-501596 A | 1/2014 |
| JP | 2014-128456 A | 7/2014 |
| JP | 2014-210180 A | 11/2014 |
| JP | 2015-112475 A | 6/2015 |
| JP | 2015-131028 A | 7/2015 |

OTHER PUBLICATIONS

International Search Report (PCT/ISA/210) issued in PCT Application No. PCT/JP2016/084099 dated Feb. 14, 2017 with English translation (four (4) pages).
Japanese-language Written Opinion (PCT/ISA/237) issued in PCT Application No. PCT/JP2016/084099 dated Feb. 14, 2017 (five (5) pages).

* cited by examiner

PHOTON-COUNTING CT APPARATUS

TECHNICAL FIELD

The present invention relates to an X-ray CT (Computed Tomography) apparatus (hereinafter referred to as a PCCT apparatus) having a photon counting mode and, more particularly, pertain to a technology for more accurate data acquisition.

BACKGROUND ART

An X-ray CT apparatus acquires data resulting from X-ray transmission through an object, while rotating a pair of an X-ray source and an X-ray detector which are placed facing each other with the object positioned therebetween and reconstructs a tomographic image (hereinafter referred to as a CT image) of the object through calculation and the apparatus is used as, inter alia, inspection equipment for industrial use and security application and diagnostic imaging equipment for medical application.

One type of X-ray CT apparatus for medical application is a PCCT apparatus provided with a photon counting mode. The PCCT apparatus counts photons of X-ray (X-ray photons) that transmitted through an object per element to be detected by a photon counting scheme based X-ray detector, as found in, e.g., PLT 1. Through this it is possible to obtain, for example, a spectrum enabling presumption of elements constituting an internal tissue of the object through which X-ray transmitted and to obtain an X-ray CT image in which element level differences are visually represented in detail.

Also, the PCCT apparatus is able to obtain X-ray intensity per energy value by discriminating counted X-ray photons by energy value. Using this, the PCCT apparatus extracts only X-rays within a particular range of energy and makes imaging of the X-rays, which may be used for diagnosis.

The X-ray CT apparatus images an object from different angles, while rotating the X-ray source; this process involves a fluctuation in results of temporal integration in a rotational direction due to errors in spacing between notches in the rotational direction (this fluctuation will be referred to as a temporal fluctuation in the rotation direction hereinafter). That is, errors occur with intervals, for each of which individual pieces of data in the rotational direction are integrated (each of the intervals will be referred to as a view). Because view length varies, there is a larger number of data in a longer interval and, conversely, there is a smaller number of data in a shorter interval. Moreover, the X-ray intensity of the X-ray source fluctuates over time. Because of these errors, an artifact is generated in an image which is obtained with the X-ray CT apparatus. For preventing such artifact, the X-ray CT apparatus uses a reference detector to reduce such errors. In particular, an X-ray detector for reference is placed in a location where X-ray does not transmit through an object and performs measurement in the same timing as an X-ray detector located to detect X-ray that transmitted through the object; thereby, data is acquired with regard to a temporal fluctuation in the rotational direction due to errors in spacing between notches in the rotational direction and a fluctuation pertaining to the X-ray source. Then, corrections are made with a ratio between the outputs of the X-ray detector and the reference detector with respect to each view; thus, these two kinds of errors can be corrected.

CITATION LIST

Patent Literature

PLT 1: Japanese Patent Application Laid-Open No. 2015-131028

SUMMARY OF INVENTION

Technical Problem

The PCCT apparatus also involves a temporal fluctuation in the rotational direction due to errors in spacing between notches in the rotational direction and a fluctuation pertaining to the X-ray source, as is the case for the X-ray CT apparatus noted above. Hence, a reference detector is required and, moreover, the PCCT apparatus acquires data per energy range and this makes it necessary to take X-ray fluctuations per energy range into account. However, a photon counting scheme based detector involves detection errors because of pile-up that means deviations per energy range attributed to detector characteristics and errors attributed to pile-up are also involved in data acquired by the reference detector; therefore, there is a need for error reduction in a different way than for conventional X-ray CT apparatus.

The present invention has been developed in consideration of the problem noted above and an object thereof is to provide a PCCT apparatus capable of correcting different kinds of fluctuations with high precision.

Solution to Problem

In order to achieve the foregoing object, the present invention provides a photon-counting CT apparatus comprising an X-ray irradiation unit which delivers X-rays, a photon counting scheme based X-ray detection unit which detects the X-rays, a data acquisition unit which counts X-ray photons detected by the X-ray detection unit for each of energy ranges which are predetermined divisions of energy, thus acquiring measurement information for each of the energy ranges, a reference detection unit which measures fluctuations in X-rays delivered from the X-ray irradiation unit, and a time measuring unit which measures temporal fluctuations in a rotational direction of the X-ray irradiation unit.

Advantageous Effects of Invention

According to the present invention, measurements with higher precision can be accomplished by measuring temporal fluctuations in the rotational direction in the PCCT apparatus more accurately.

DESCRIPTION OF EMBODIMENTS

Different embodiments of the present invention will be described in accordance with the drawings. In all drawings to explain the embodiments, those having a same function are assigned an identical reference designator and duplicated description thereof is dispensed with. In addition, in the present invention, different kinds of fluctuations occurring in the PCCT apparatus are corrected with high precision, such as a temporal fluctuation in a rotational direction, a fluctuation pertaining to the X-ray source, and a fluctuation attributed to pile-up. Here, the temporal fluctuation in the rotational direction means a fluctuation in results of temporal integration in the rotational direction and the fluctuation pertaining to the X-ray source means a fluctuation in an X-ray irradiance level and an X-ray spectrum of the X-ray source.

First Embodiment

A first embodiment is an embodiment of a PCCT apparatus that is provided with a reference detection unit and a time measuring unit which measures time, corrects a temporal fluctuation in the rotational direction with time measured by the time measurement unit, and corrects fluctuations pertaining to the X-ray source and pile-up through the use of measurement data acquired by the reference detection unit. In the measurement data, temporal fluctuations in the rotational direction have been corrected with measured time. More specifically, the present embodiment is an embodiment of a PCCT apparatus that is configured such that the apparatus is equipped with an X-ray irradiation unit which delivers X-rays, a photon counting scheme based X-ray detection unit which detects X-rays, a data acquisition unit which counts X-ray photons detected by the X-ray detection unit for each of energy ranges which are predetermined divisions of energy, thus acquiring measurement information per energy range, a reference detection unit which measures fluctuations in X-rays delivered from the X-ray irradiation unit, and a time measuring unit which measures temporal fluctuations in the rotational direction of the X-ray irradiation unit, and is further equipped with a correction unit which corrects measurement data measured by the reference detection unit, based on time measurement data measured by the time measuring unit.

In the present embodiment, as an X-ray CT apparatus, a PCCT apparatus having a photon counting scheme based X-ray detector is used, instead of a conventional current mode measurement based, integration type detector. In the PCCT apparatus, photons derived from X-rays that transmitted through an object (X-ray photons) are counted by the photon counting scheme based X-ray detector. Individual X-ray photons have different energy values. By counting the X-ray photons and discriminating them per predetermined energy range, the PCCT apparatus is capable of obtaining X-ray intensity corresponding to the counts of X-ray photons per energy range as measurement information.

[Outline Structure of the X-ray CT Apparatus]

Figure 1:
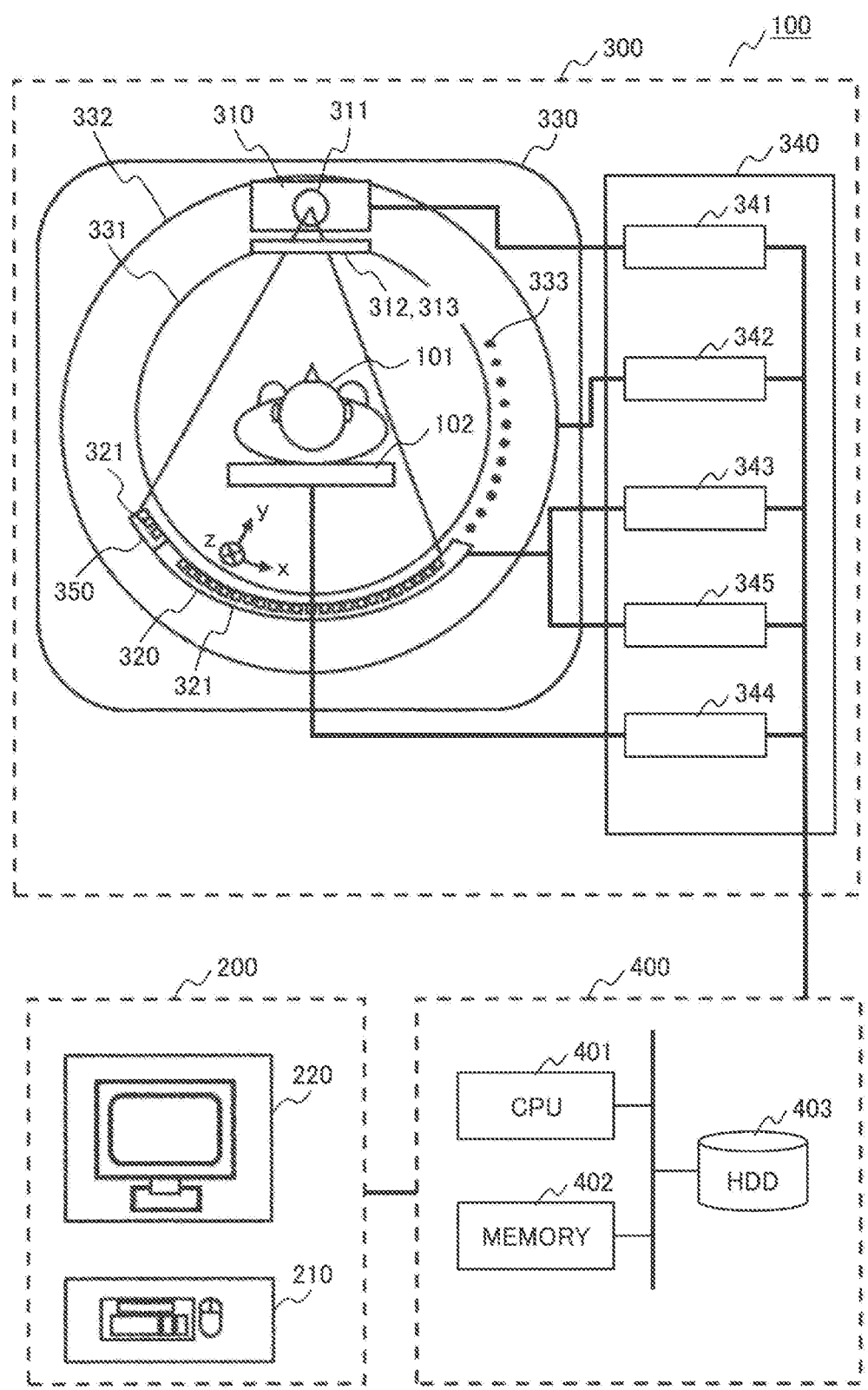
FIG. 1 is a diagram depicting one example of a structure of a PCCT apparatus pertaining to first through fourth embodiments.

One example of outline structure of the PCCT apparatus of the present embodiment is described with FIG. 1. As depicted in FIG. 1, the PCCT apparatus 100 of the present embodiment includes a user interface (hereinafter referred to as UI) section 200, a measurement section 300, and a computation section 400.

The UI section 200 accepts input from a user and presents a result of processing performed by the computation section 400 to the user. For this purpose, the UI section 200 includes an input device 210 such as a keyboard and a mouse, a display device such as a monitor, and an output device 220 such as a printer. The display device is configured using a liquid crystal display, a CRT (Cathode Ray Tube), or the like. Now, the output device 220 may be configured such that its display has a touch panel function, so that it can be used as the input device 210.

[Measurement Section]

The measurement section 300 irradiates an object 101 with X-ray and measures X-ray photons that transmitted through the object 101, according to control by the computation section 400. The measurement section 300 includes an X-ray irradiation unit 310, an X-ray detection unit 320, a reference detection unit 350 placed beside the X-ray detection unit in a position where incident X-rays arrive without transmitting through the object, a gantry (mount) 330, a control unit 340, and a table 102 for resting the object 110 thereon.

[Gantry]

In the center of the gantry 330, there is a circular bore 331 for placing the object 101 and the table for resting the object 101 thereon. Inside the gantry 330, a rotary plate 332 to mount an X-ray tube 311, which will be described later, and the X-ray detection unit 320 equipped with an X-ray detector 321 thereon and a drive mechanism for rotating the rotary plate 332 are disposed and they are controlled by a gantry controller 342, which will be described later, in the control unit 340.

Furthermore, the rotary plate 332 is engraved with notches 33 in the rotational direction and integration is performed upon the transit of each notch 333. More specifically, traversing a notch 333 causes a signal to be input to a detection controller 343, which will be described later, in the control unit 340 and a command for data processing is issued according to this signal. Time it takes the rotary plate 332 to rotate by one turn depends on a parameter entered by the user via the UI section 200. In the present embodiment, time it takes the rotation is assumed to be, for example, 1.0 s/turn. The number of times that an image is captured by the measurement section 300 for one turn is, for example, 900 times and image capturing is performed once each time the rotary plate 332 rotates by 0.4 degrees.

Respective specifications are not to be limited to these values and may be varied according to the structure of the PCCT apparatus 100. Now, spacing between the notches 333 has errors, as noted previously, and this produces a temporal fluctuation in the rotational direction.

It is assumed herein that, for the bore 331, its circumferential direction is direction x, its radial direction is direction y and a direction in which these axes bisect at right angles is direction z, as marked in FIG. 1. Generally, direction z corresponds to the body axis of the object 101.

[X-ray Irradiation Unit]

The X-ray irradiation unit 310 generates X-rays and delivers the generated X-rays to the object 101. The X-ray irradiation unit 310 is equipped with the x-ray tube 311, an X-ray filter 312, and a bowtie filter 313.

The X-ray tube 311 delivers an X-ray beam to the object 101 by a high voltage which is supplied according to control by an irradiation controller 341 which will be described later. The x-ray beam that is delivered spreads out with a fan angle and a cone angle. The X-ray beam is delivered to the object 101 along with rotation of the rotary plate 332 of the gantry 330.

The X-ray filter 312 adjusts the quality of X-rays delivered from the X-ray tube 311. That is, it modifies an X-ray spectrum. The X-ray filter 312 in the present embodiment attenuates X-rays delivered from the X-ray tube 311 so that X-rays to be delivered to the object 101 from the X-ray tube 311 will have a predetermined energy distribution. The X-ray filter 312 is used to optimize dosage that a patient that is the object 101 receives. For this purpose, it is designed to intensify the radiation dose in necessary energy ranges.

The bowtie filter 313 suppresses dosage in peripheral portions. Taking advantage of that a human body that is the object 101 has an elliptical shape, this filter is used to optimize dosage by intensifying the radiation dose around the center of the body and decreasing the radiation dose in peripheral portions.

[X-ray Detection Unit, Reference Detection Unit]

Each time an incident X-ray photon has come, the X-ray detection unit 320 outputs a signal by which an energy value of the X-ray photon can be measured. The X-ray detection unit 320 is equipped with the X-ray detector 321.

Figure 2A:
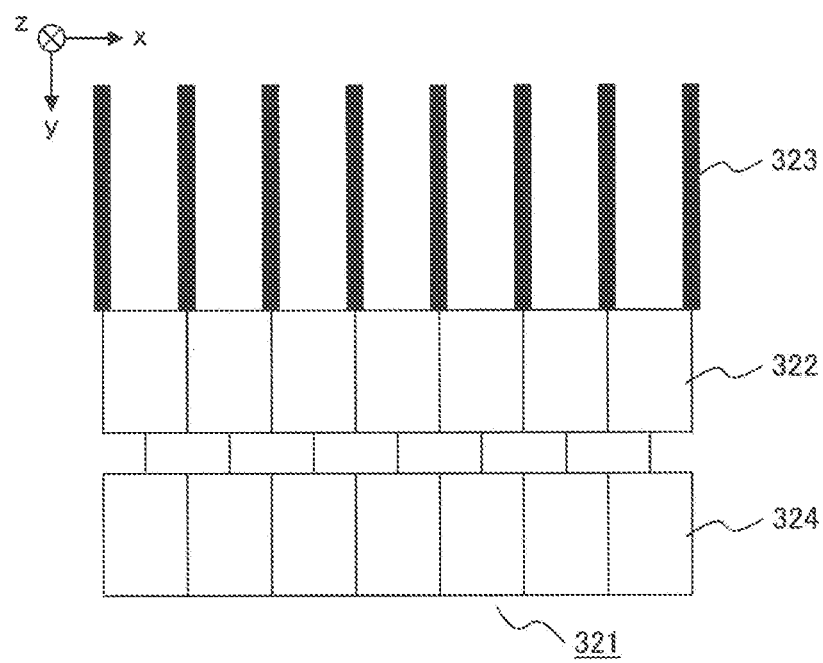
FIGS. 2A and 2B are diagrams illustrating one example of an X-ray detector pertaining to the first embodiment.
Figure 2B:
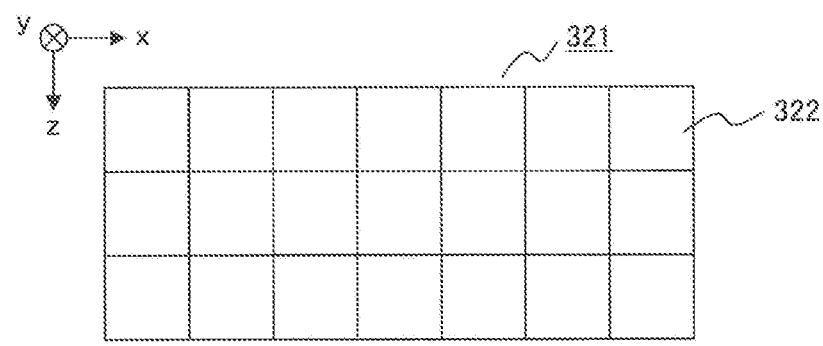

FIG. 2 exemplifies a part of the X-ray detector 321. As can be seen in a cross-sectional structure and a planar structure in FIGS. 2(*a*) and (*b*), the X-ray detector 321 is equipped with a plurality of detection elements 322, a counting circuit 324 electrically connected with each detection element 322, and a collimator 323 which confines an incident direction to the X-ray detector 321.

The reference detection unit 350 also has the same structure as the X-ray detector 321 exemplified in FIG. 2. The X-ray detection unit 320 is the one in which the structure, a part of which is depicted in FIG. 2(*a*), is duplicated in direction x. The reference detection unit 350 may employ one of X-ray detectors at an edge of the X-ray detection unit 320. In that case, care should be taken to avoid that a part of the object will not come in an effective field of view (FOV). Conversely, the X-ray detection unit 320 and the reference detection unit 350 may be well separated from each other to avoid an overlap with the FOV. Also, the X-ray detector 321 may have a structure in which many detector elements 322 are arranged two-dimensionally in directions x and z in positions having a substantially equal distance from a plurality of X-ray generation points of the X-ray tube 311, as depicted in FIG. 2(*b*); this applies to both the X-ray detection unit 320 and the reference detection unit 350.

Now, to facilitate manufacturing, the X-ray detector 321 may be configured by manufacturing a plurality of detector modules which are planar X-ray detectors and arranging them so that planar center portions form an arc to make a pseudo arc arrangement.

For incident X-rays received by the respective detection elements 322, every incident X-ray photon is converted to an electric signal (analog signal) of one pulse by each counting circuit 324 electrically connected. An electric signal resulting from the conversion is input to the computation section 400 which will be described later.

In the present embodiment, for the detection elements 322, for example, a Cadmium Telluride (CdTe) semiconductor element that directly converts an incident X-ray photon to an electric signal is used. Now, for the detection elements, a Scintillator that emits fluorescence by receiving X-ray and a photo diode that converts fluorescence to electricity may be used.

The number of the detection elements 322 of the X-ray detector 321 in direction x, namely, the number of channels is, for example, 1000 elements. Size of each detection element in direction x is, for example, 1 mm.

In addition, the distance between the X-ray generation points of the X-ray tube 311 and the X-ray incident surface of the X-ray detector 321 is, for example 1000 mm. The diameter of the bore 331 of the gantry 330 is, for example, 700 mm.

Now, as is the case for the gantry 330, respective specifications of the X-ray detection unit 320 are not to be limited to these values and may be varied according to the structure of the PCCT apparatus 100.

[Control Unit]

The control unit 340 includes an irradiation controller 341 which controls delivery of X-ray irradiation from the X-ray tube 311, a gantry controller 342 which controls driving to rotate the rotary plate 332, a table controller 344 which controls driving of the table 102, a detection controller 343 which controls X-ray detection by the X-ray detector 321, and a time measuring instrument 345 which is a time measuring unit to measure time in the rotational direction. When a signal of measured time in the rotational direction, generated upon traversing a notch 333, which is shown in the description regarding the gantry 330, is input to the detection controller 343, the time measuring instrument 345 receives the signal at the same time and stores the measured time in the rotational direction.

All these controllers in the control unit 340 operate according to control by a measurement control unit 420 in the computation section 400 which will be described later.

[Computation Section]

Figure 3:
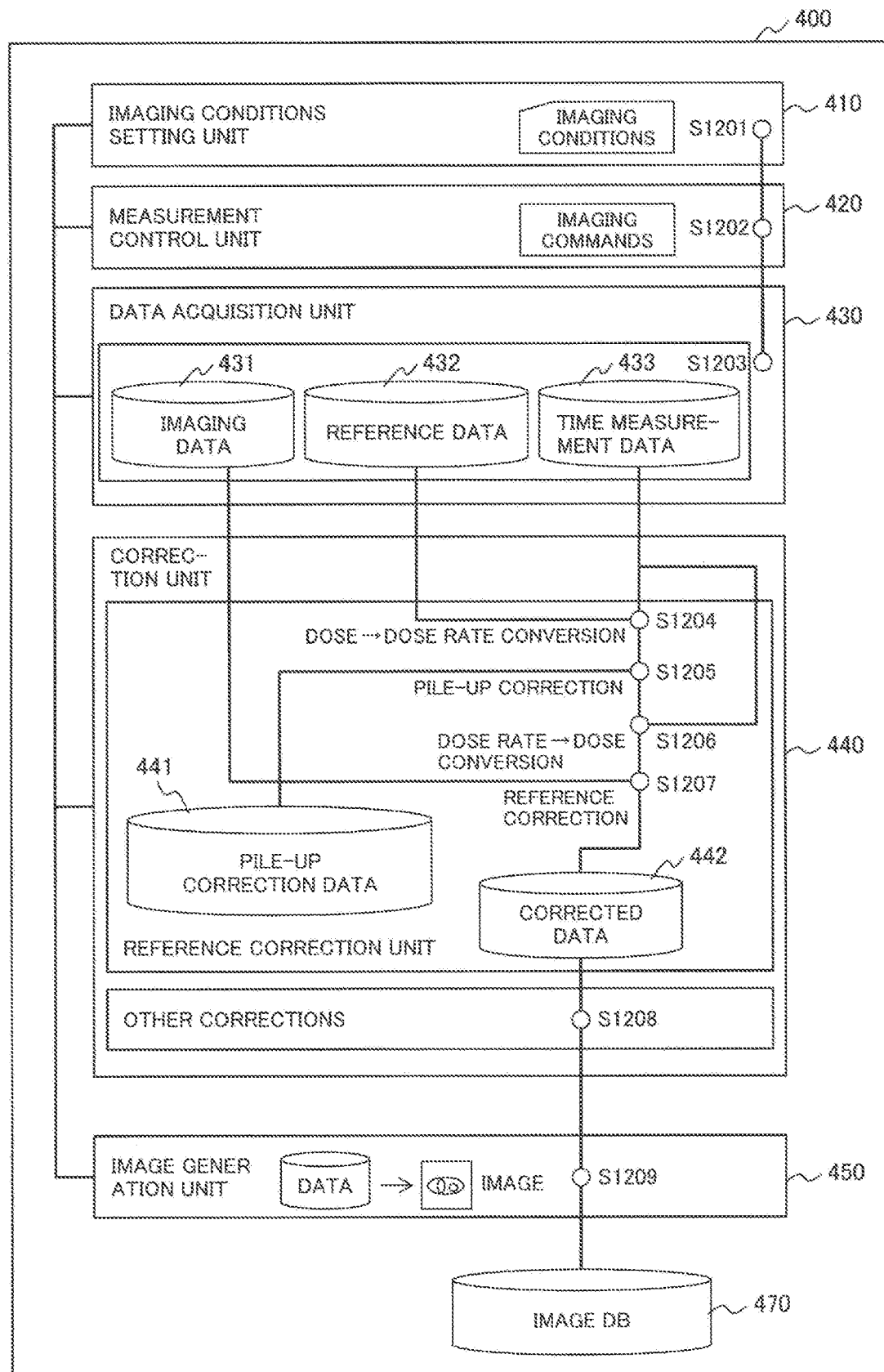
FIG. 3 is a diagram illustrating, by way of example, functional blocks of a computation section of the PCCT apparatus and a processing flow pertaining to the first embodiment.

FIG. 3 depicts a functional block diagram of the computation section 400 in the present embodiment. The computation section 400 exerts an overall control of the operation of the PCCT apparatus 100 and processes data acquired by the measurement section 300, thus imaging the object. As depicted in FIG. 3, the computation section 400 includes an imaging conditions setting unit 410, a measurement control unit 420, a data acquisition unit 430, a correction unit, and an image generation unit 450, each of which will be detailed below.

As for its hardware structure, the computation section 400 is equipped with a central processing unit (CPU) 401, a memory 402, and a hard disk drive (HDD) device 403, as depicted in FIG. 1. For instance, the central processing unit 401 loads a program which has been retained beforehand in the HDD device 403 to the memory 402 and executes the program, thus implementing each function.

All or some of the functions of the computation section 400 may be implemented by an integrated circuit such as an ASIC (Application Specific Integrated Circuit) or an FPGA (Field Programmable Gate Array) instead of programs.

In addition, data for use in processing, data generated in processing, data resulting from processing, etc. are stored in the HDD device 403. Now, results of processing are output to the output device 220 such as a display device in the UI section 200

[Image Conditions Setting Unit]

The imaging conditions setting unit 410 accepts and sets imaging conditions that are specified by a user with the UI section 200. For instance, the imaging conditions setting unit 410 displays an entry screen for accepting image conditions on the display device and accepts imaging conditions via the entry screen. The user inputs imaging conditions via the entry screen by operating the input device 210, e.g., a mouse, keyboard, touch panel, etc.

Imaging conditions that may be set are, for example, a tube current and a tube voltage of the X-ray tube 311, a scope of the object 101 to be imaged, type of the X-ray filter 312, shape of the bowtie filter 313, resolution, etc.

Now, the user may not always have to input imaging conditions every time through the use of the UI section 200. For instance, typical imaging conditions that have been pre-stored in the HDD 403 or the like may be read out and used.

The measurement control unit 420 controls the control unit 340 and carries out a measurement according to imaging conditions set as specified by the user.

In particular, the measurement control unit 420 instructs the table controller 344 to move the table 102 in a direction perpendicular to the rotary plate 332 and stop at a point when a position for imaging to be performed using the rotary plate 332 has become coincident with the set position for imaging. This completes positioning the object 101.

Also, the measurement control unit 420 instructs the gantry controller 342 to actuate a drive motor and start to rotate the rotary plate 332 at the same timing as instructing the table controller 344.

When the rotary plate 332 has entered a state that it rotates at a steady speed and positioning the object 101 is complete, the measurement control unit 420 instructs the irradiation controller 341 as to timing to start X-ray irradiation to be delivered from the X-ray tube 311 and instructs the detection controller 343 as to timing to start imaging by the X-ray detector 321. Thereby, the measurement control unit 420 executes X-ray irradiation and detection of X-ray photons by the detector and initiates a measurement.

By repeating these instructions to the control unit 340, the measurement control unit 420 executes measurement throughout the imaging scope. Now, the measurement control unit 420 and the control unit 340 may implement control to carry out imaging, while moving the table 102 as is the case for Helical Scan which has been known publicly.

[Data Acquisition Unit]

The data acquisition unit 430 counts X-ray photons derived from X-rays detected by the X-ray detector 321 for each of predetermined energy ranges, thus acquiring, as imaging data 431, count values for each of the energy ranges, namely, projection data corresponding to measurement information. The data acquisition unit 430 in the present embodiment is equipped with a Data Acquisition System (DAS, hereinafter referred to as DAS) and this DAS performs counting X ray-photons detected by the measurement section 300, thus acquitting count values as imaging data 431. Also, the data acquisition unit 430 acquires outputs of the reference detection unit 350 as reference data 432 and acquires outputs of the time measuring instrument 345 as time measurement data 433.

The DAS acquires a value of energy of each of X-ray photons detected by the X-ray detector 321 and, according to the value of energy, increments a count value that is a counting result in one of energy bins provided per energy range. The energy bins are storage areas which are set per energy range bins.

Respective energy ranges are those into which a whole range of energy from 0 keV to a maximum value of energy of the X-ray tube 311 was divided in units of a predetermined width of energy ΔB. Given that the predetermined width of energy ΔB is, for example, 10 keV and the maximum value of energy is, for example, 140 keV, there are seven ranges of energy into which the whole range of energy was divided: B1 (0 to 20 keV), B2 (20 to 40 keV), B3 (40 to 60 keV), B4 (60 to 80 keV), B5 (80 to 100 keV), B6 (100 to 120 keV), and B7 (120 to 140 keV). According to the value of energy of a detected X-ray photon, the DAS serially increments the counting result in an energy bin allocated for a range of energy in which the value of energy falls.

Figure 4:
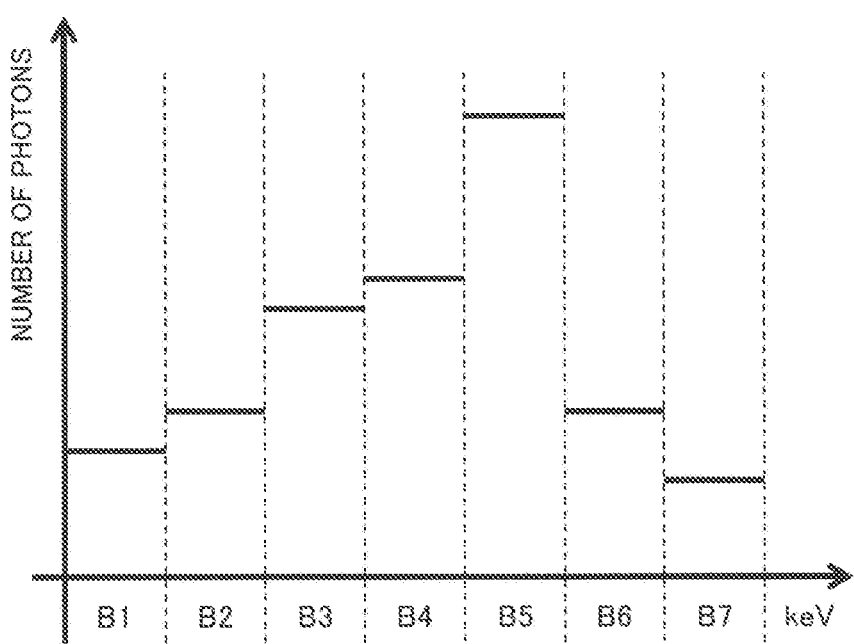
FIG. 4 is a diagram to illustrate one example of the X-ray detector pertaining to the first embodiment.

FIG. 4 illustrates one example of results of counting. As is obvious in this figure, the abscissa plots respective energy ranges B1 to B7 and the ordinate plots the number of photons for each of the energy ranges. In this way, the data acquisition unit 430 counts the number of X-ray photons per energy range. As seen in FIG. 4, obtained results indicate a distribution of energy values (units: keV) of X-ray photons. Therefore, the data acquisition unit 430 also thus obtains an energy distribution, or a spectrum of X-rays detected by the X-ray detector 321. The data acquisition unit 430 outputs imaging data 431 corresponding to obtained results as measurement information.

Now, the whole range of energy, respective energy ranges, i.e., the energy ranges for each of which each energy bin is allocated, and the number of bins are set beforehand as specified by the user or in other manners. In addition to this imaging data 431, the data acquisition unit 430 acquires reference data 432 and time measurement data 433 which will be described later.

[Correction Unit]

The correction unit 440 carries out correction processing through the use of imaging data 432, reference data 432, and time measurement data 433 acquired by the data acquisition unit 430. The correction processing to be performed here includes, for example, linearity correction of a reference correction circuit using reference data 432, logarithmic conversion processing, offset processing, sensitivity correction, beam hardening correction, etc. Now, as for methods for corrections other than a reference correction, publicly known techniques are to be used here. A method for the reference correction will be set forth in descriptions of "flow of preprocessing for imaging" and "flow of imaging process" provided later.

[Image Generation Unit]

The image generation unit 450 reconstructs an X-ray CT image from the number of photons stored in the respective energy bins, i.e., imaging data 431. Such image is, for example, reconstructed by executing a Log conversion of measurement information corresponding to the number of X-ray photons. For the reconstruction, it is possible to use one of diverse methods such as FeldKamp method and successive approximation, which have been known publicly. Now, imaging data stored in all energy bins need not be used for image generation. It may be only required to use imaging data corresponding to count values stored in energy bins allocated for certain energy ranges predetermined.

[Flow of Preprocessing for Imaging]

Preprocessing for actually imaging the object through the use of the respective items described above is described here. Prior to imaging, data necessary for various corrections is acquired. As for methods for corrections other than a reference correction, publicly known techniques are assumed to be used. Descriptions are provided here as to how to acquire reference data 432 necessary for the reference correction.

Before acquisition, data necessary for the reference correction by the correction unit 440 is pile-up correction data 441. The pile-up correction data 441 is data representing a relation between dose rate data and the amount of change in the count values, i.e., measurement information attributed to pile-up. Creating the pile-up correction data 441 can be implemented by changing the dose rate of irradiation by the X-ray irradiation unit 310 and taking measurements in advance as to how the signal amount detected by the reference detection unit 350 changes accordingly. Because the amount of pile-up typically increases by augmenting the dose rate of irradiation by the X-ray irradiation unit 310, the counts will offset lower than a value proportional to the dose rate. The dose rate also changes when correction data is acquired. Therefore, imaging should be performed for a sufficiently long time with regard to each data in response to a change in the dose rate to create pile-up correction data 441 in which an amount of pile-up correction is given to compensate for the above-mentioned offset from the proportional value.

Figure 13:
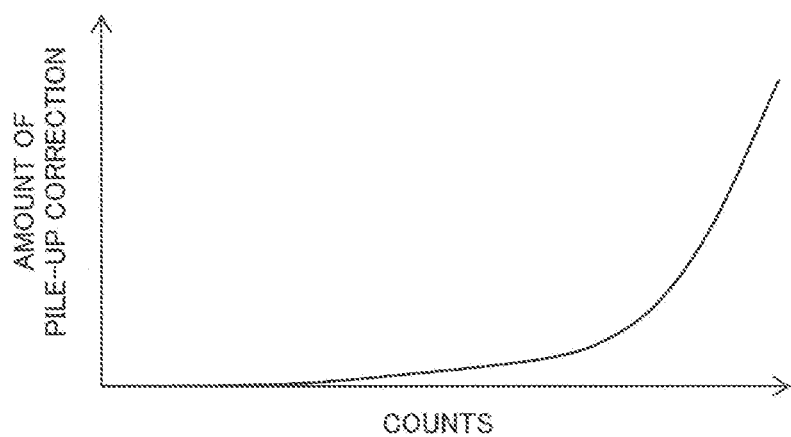
FIG. 13 is a diagram illustrating one example of pile-up correction data in the PCCT apparatus pertaining to the first embodiment.

FIG. 13 illustrates one example of pile-up correction data 441 in the PCCT apparatus of the present embodiment. In this figure, the abscissa plots counts and the ordinate plots the amount of pile-up correction. Measured count values are multiplied by this amount of pile-up correction depending on the counts.

[Flow of Imaging Process]

Then, a flow of an imaging process to be performed by the computation section 400 is described. FIG. 3 is a processing flow of the imaging process according to the present embodiment. Pile-up correction data 441, for example, as illustrated in FIG. 13, is assumed to have been created beforehand in the flow of preprocessing for imaging described previously.

First, the imaging conditions setting unit 410 accepts imaging conditions from the user via the UI section 200 (step S1201). Input of imaging conditions that may be accepted here includes a tube voltage, a tube current, type (thickness and material) of the X-ray filter 312, shape of the bowtie filter 313, etc.

Then, the measurement control unit 420 executes measurements (S1202) according to the imaging conditions set at step S1201 and the data acquisition unit 430 acquires various sets of data (step S1203). By acquiring these sets of data, the data acquisition unit 430 gets imaging data 431 acquired through the X-ray detection unit 320, which includes information on the object 101, reference data 432 acquired through the reference detection unit 350, and time measurement data 433 acquired through the time measuring instrument 345 which is the time measuring unit.

After that, the correction unit 440 corrects the imaging data 431 acquired by the data acquisition unit 430. First, the correction unit executes a conversion of dose→dose rate, which converts a dose per view to a dose per unit time, or a dose rate with respect to each energy range in the reference data 432 (step S1204). Now, herein, a sign "→" denotes converting a left-hand value to a right-hand value. This is because pile-up depends on a dose rate, but not a dose and a dose per view is not equivalent to a dose rate, since time for a view fluctuates or varies among views. As for a way of the conversion, a conversion to a dose rate is made by dividing a dose for each view by time per view based on the time measurement data 433.

Then, the correction unit executes a pile-up correction, using reference data converted to a dose per unit time, or a dose rate (step S1205). As for a way of the pile-up correction, execute corrections, as described previously, of counts for each energy range, acquired through the reference detection unit 350, using pile-up correction data 441 which is created in the flow of preprocessing for imaging and one example of which is illustrated in FIG. 13. The correction unit 440 corrects the dose rate data, based on the pile-up correction data obtained by measuring beforehand the dose rate data and the amount of change in the count values, i.e., measurement information attributed to pile-up. Here, corrected reference data is data per unit time, whereas imaging data 431 acquired by the data acquisition unit is data per view. Hence, with respect to the corrected reference data, the correction unit executes a conversion of dose rate->dose (step S1206), which is a reverse operation to step S1204. In particular, a conversion to a dose is made by multiplying a dose rate for each view by time per view based on the time measurement data 433. Now, without making the conversion to a dose at step S1206, matching the units of corrected reference data with the units of imaging data may be effected by executing the conversion of dose→dose rate as done at step S1204 with respect to the imaging data 431.

After this units matching, the correction unit executes a reference correction with respect to the imaging data (step S1207). Based on the corrected count values for each energy range, acquired through the reference detection unit, which have been corrected at step S1206, the correction unit corrects fluctuations in the count values of X-rays and obtains corrected data 442. In the case of commonly used X-ray CT apparatus, data as the sum of data pieces acquired for all energy ranges can only be acquired. Because the PCCT apparatus takes measurements per energy range, corrections cannot be performed properly unless measurements are taken of X-ray fluctuations per energy range. Hence, the correction unit executes a reference correction using measurements data taken per energy range.

Through the above process, it is enabled to correct fluctuations pertaining to the X-ray source and temporal fluctuations in the rotational direction. After that, the correction unit executes other corrections (step S1208). Although corrections other than the reference correction are brought together in step 1208, these corrections may be executed before the reference correction as required or a part of the corrections may be executed before the reference correction and the remaining part of the corrections may be executed after the reference correction. The image generation unit 450 generates an image using data eventually obtained through the corrections and stores the image into an image DB 470 (step S1209); then, the process finishes.

According to the PCCT apparatus of the present embodiment, it is possible to measure temporal fluctuations in the rotational direction more accurately and correct fluctuations pertaining to the X-ray source, while correcting deviations per energy range attributed to detector characteristics, which occur in the reference detection unit, especially through steps S1204 to S1207; therefore, corrections can be performed with high precision.

Second Embodiment

In the first embodiment, a semiconductor detector is used for the reference detection unit 350 to enable setting of energy ranges. However, if correspondence between the signal amount detected by the reference detection unit 350 and the signal amount detected by all the X-ray detectors 321 belonging to the X-ray detection unit 320 is known, it is also possible to use an integration type detector as the reference detection unit 350. Use of an integration circuit as the integration type detector has an advantage that there is no need for correcting pile-up or the like specific to counting circuits. The second embodiment describes an embodiment configured such that such an integration type detector is used as the reference detection unit and integrated reference data is acquired, according to FIG. 5 and FIG. 6.

The second embodiment is an embodiment of a PCCT apparatus configured as follows: the reference detection unit 350 is an integration type detector; with regard to X-rays delivered from the X-ray irradiation unit, the correction unit obtains beforehand a relation between signal amounts detected by the reference detection unit 350 and measurement information per energy range obtained through the X-ray detection unit 320 and makes corrections of measurement information per energy range from a relation between measurement information per energy range obtained through the X-ray detection unit 320 when imaging an object is performed and the previously obtained measurement information and a relation between signal amounts detected by the reference detection unit during imaging and the previously obtained signal amounts detected by the reference detection unit. Changes from the first embodiment reside in the X-ray detector, the reference detection unit, the flow of preprocessing for imaging, and the flow of the imaging process. About these, what has been changed is described below.

[X-ray Detection Unit, Reference Detection Unit]

Figure 5A:
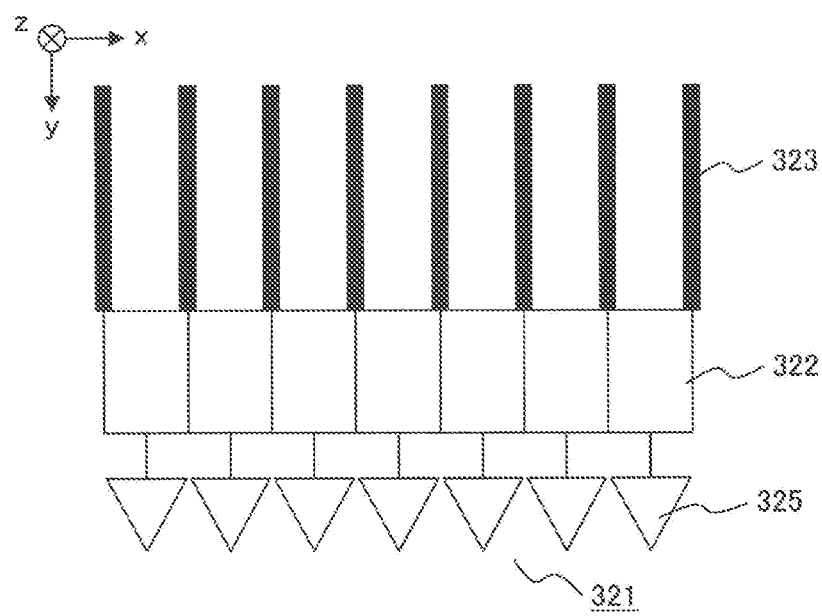
FIGS. 5A and 5B are diagrams illustrating one example of the X-ray detector pertaining to the second embodiment.
Figure 5B:
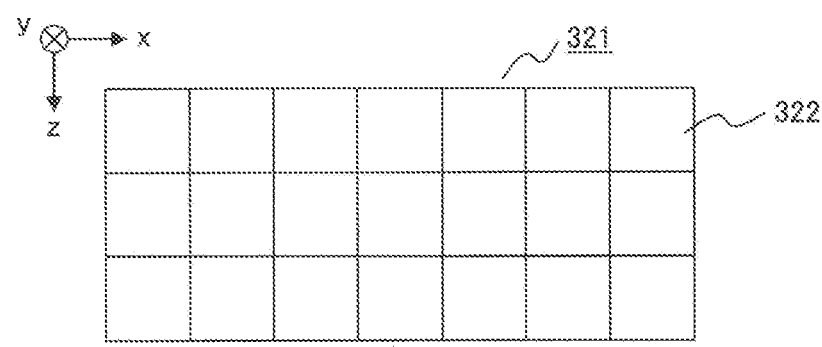

In the present embodiment, as depicted in FIG. 5, the X-ray detector 321 of the reference detection unit 350 employs an integration circuit 325 instead of the counting circuit 324 in FIG. 2. The integration circuit 325 is a circuit that is used in conventional X-ray CT apparatus and this circuit sums up signal amounts of all incident X-rays for each view and outputs the sum. Hence, pile-up does not occur in the integration circuit 325, but data per energy range cannot be acquired.

However, in the case of PCCT apparatus, corrections must be made according to a dose rate per energy range; therefore, with regard to integrated data as well, a conversion from an integrated dose per view to an integrated dose rate has to be made before corrections. For this reason, changes are made to correction computation. These changes are set forth below.

[Flow of Preprocessing for Imaging]

In the case where the integration type detector is sued for the reference detection unit 350, as described above, amounts of correction per energy range have to be obtained from the signal amount detected by the reference detection unit 350. However, because the integration type detector is unable to acquire data per energy range, such data has to be obtained beforehand. Causes of fluctuations in signals detected by the reference detection unit 350 are fluctuations pertaining to the X-ray source, that is, fluctuations in the X-ray intensity and the dose rate of the X-ray tube 311 and temporal fluctuations in the rotational direction, that is, fluctuations as to a time integration result in the rotational direction, as described previously. Even the integration type reference detection unit 350 takes measurements including two kinds of fluctuations mentioned above. Fluctuations in the X-ray intensity of the X-ray tube 311, if any, may change proportions among energy ranges and this change may vary depending on characteristics of the X-ray tube 311. On the other hand, temporal fluctuations in the rotational direction do not change proportions of signal amounts among energy ranges. Hence, it is required to create correction data, taking these two kinds of fluctuations into account.

A measurement method for the second embodiment is set forth below. First, set the X-ray tube 311 to one of settable doses. In addition, remove both the bowtie filter 313 and the X-ray filter 312. Carry out X-ray irradiation in this condition and measure both incident signals received by the reference detection unit 350 and the X-ray detection unit 320. Categorize signals detected by the integration circuit 325 of the reference detection unit 350 according to different amounts of signal fluctuation and calculate dose rates per energy range of X-rays acquired by the X-ray detection unit 320 with respect to each of the amounts of fluctuation by which the signals were categorized. In this regard, because a time deviation may occur among views, an adjustment may be made so that time for each view will be equal to a criterion time, using time measurement data of the time measurement instrument 345. Averaging for each energy range is performed in this way; the reason for this is that fluctuations pertaining to the X-ray tube 311 do not always occur equally throughout the whole range of energy. By preparing correction data in this way, differences of fluctuations per energy range can be smoothened. By carrying out this operation for all the settable doses, create conversion data from obtained integration data to each energy range, that is, create integration→energy range conversion data 443.

A concrete example of a method for creating this integration→energy range conversion data 443 is set forth. Carry out X-ray irradiation with both the bowtie filter 313 and the X-ray filter 312 removed and measure both incident signals received by the reference detection unit 350 and the X-ray detection unit 320, as noted previously. Divide thus measured data by time per view based on time measurement data 433 and convert the amounts of incident signals received by both the reference detection unit 350 and the X-ray detection unit 320 to signal amounts per unit time. Categorize data resulting from this conversion according to a value (units: signal amount/time) resulting from converting the signals detected by the reference detection unit 350 to a signal amount per unit time. Because the signal amount depends on the set value of an amplifier, a practical value of the signal amount per unit time resulting from the conversion depends on device setting. Calculate an average of the amounts of incident signals per energy bin received by the X-ray detection unit 320 for each of intervals thus categorized.

When the thus obtained value resulting from the conversion of the signals detected by the reference detection unit 350 to a signal amount per unit time represents a value, the average value of the amounts of incident signals per energy bin received by the X-ray detection unit 320 becomes integration→energy range conversion data 443. For instance, given that imaging is performed with conditions of 120 kV/200 mA and 1000 views, for the apparatus set up so that 1 is given as the value resulting from conversion to a signal amount per unit time, there will be 100 counts/s in bin1, 1000 counts/s in bin2, 1000 counts/s in bin3, and 700 counts/s in bin4. When 1.01 is given as the value resulting from conversion to a signal amount per unit time, there will be 110 counts/s in bin1, 1100 counts/s in bin2, 900 counts/s in bin3, and 500 counts/s in bin4. A conversion table for such a conversion is created.

[Flow of Imaging Process]

Figure 6:
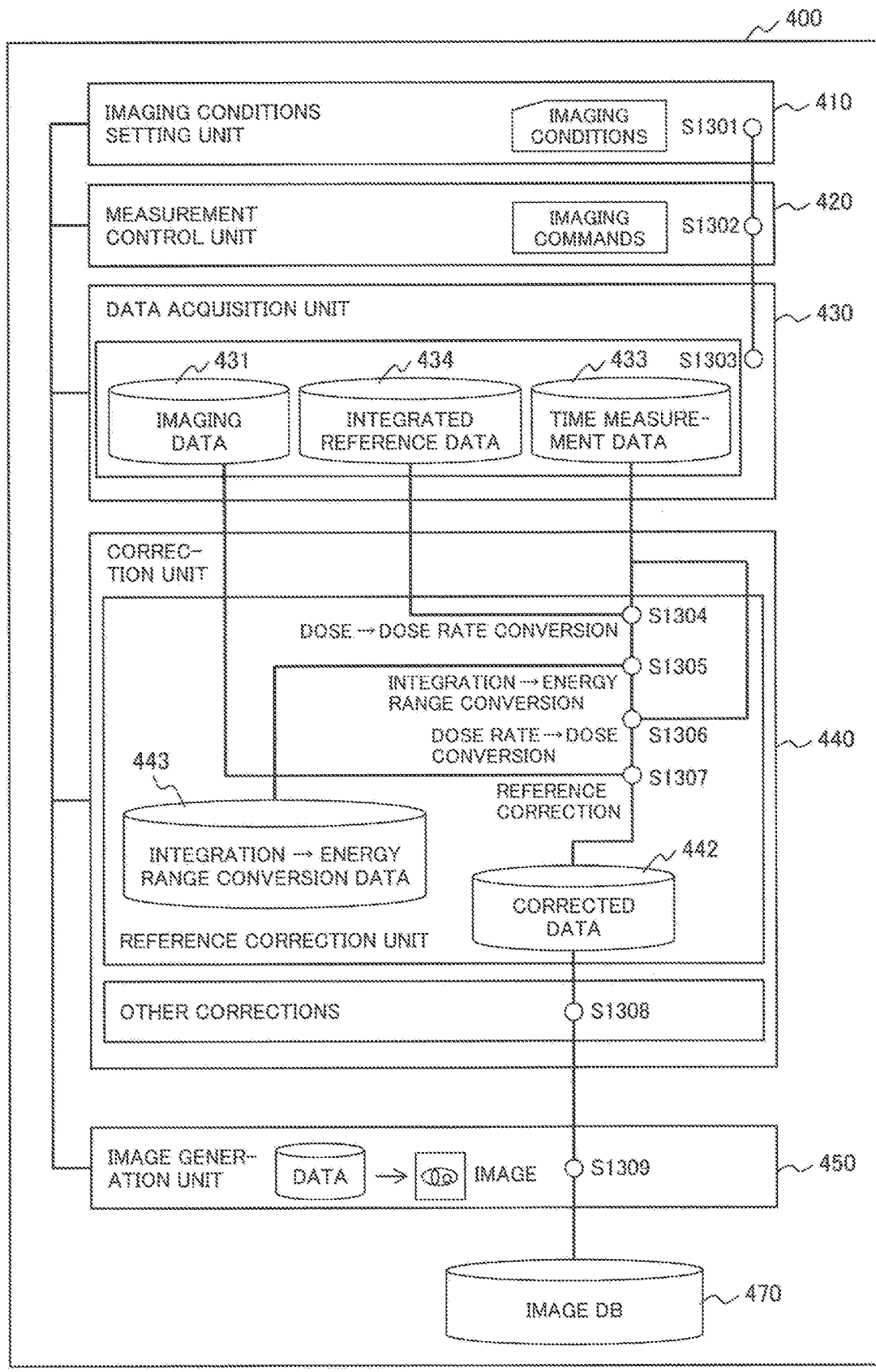
FIG. 6 is a diagram illustrating, by way of example, functional blocks of the computation section of the PCCT apparatus and a processing flow pertaining to the second embodiment.

A flow of an imaging process to be performed by the computation section 400 according to the present embodiment is described. FIG. 6 is a processing flow of the imaging process according to the present embodiment. Integration→energy range conversion data 443 is assumed to have been created beforehand in the "flow of preprocessing for imaging", as described previously.

Step S1301 to be executed by the imaging conditions setting unit 410 and step S1302 to be executed by the measurement control unit 420 are the same as step S1201 and step S1202 respectively.

The data acquisition unit 430 acquires various sets of data (step S1303). Acquired by the data acquisition unit 430 by acquiring such data, imaging data 431 acquired through the X-ray detection unit 320, which includes information on the object 101, and time measurement data 433 acquired through the time measuring instrument 345 are the same as in the previous embodiment. However, reference data acquired through the reference detection unit 350 is integrated view by view and, therefore, such data is referred to as integrated reference data 434 here.

After that, the correction unit 440 corrects the imaging data 431 acquired by the data acquisition unit 430. First, for the integrated reference data 434, the correction unit executes a conversion of dose→dose rate, which converts a dose per view to a dose per unit time, or a dose rate with respect to each energy range (step S1304). This is because fluctuations in the X-ray intensity of the X-ray tube 311 are based on a fluctuation characteristic for a unit time, as set forth in the [flow of preprocessing for imaging] section.

Then, the correction unit executes a conversion of integration→energy range described previously, using integrated reference data converted to a dose per unit time (step S1305). As for a way of the conversion of integration→energy range, create a conversion table regarding counts per energy range, based on integrated reference data for each range acquired through the reference detection unit, using integration→energy range conversion data 443 created in the [flow of preprocessing for imaging]. As is the case for the first embodiment, because data is data per unit time, the correction unit executes a conversion of dose rate→dose (step S1306), which is a reverse operation to step S1304. Now, as is the case for the previous embodiment, without making the conversion to a dose at step S1306, matching the units of corrected data with the units of imaging data may be effected by executing the same conversion to dose rate as done at step S1304 with respect to the imaging data.

After this units matching, the correction unit executes a reference correction with respect to the imaging data 431 (step S1307). Based on corrected data per energy range based on the integrated reference data acquired through the reference detection unit 350, which has been created at steps S1304 to S1306, the correction unit corrects fluctuations in the imaging data 431 corresponding to the count values of X-rays. As for a practical way of computation, perform a division of a value resulting from conversion to a signal amount per unit time, based on the integration→energy range conversion data 443. For instance, when 1 is given as the value resulting from conversion to a signal amount per unit time, a division by 100 for bin1, 1000 for bin2, 1000 for bin3, and 700 for bin4 is performed. Now, based on a criterion conversion value, a division by a ratio to that value may be performed.

Subsequently, as is the case for the first embodiment, the correction unit executes other embodiments (step S1308) and the image generation unit 450 generates an image using corrected data and then stores the image into the image DB 470 (S1309); then, the process finishes.

In the structure of the second embodiment described above, it is possible for the PCCT apparatus in which an integration detector that is free from pile-up is used as the reference detection unit to measure temporal fluctuations in the rotational direction more accurately and correct fluctuations pertaining to the X-ray source, while correcting deviations per energy range attributed to detector characteristics, which occur in the reference detection unit, especially through steps S1304 to S1307; therefore, corrections can be performed with high precision.

Third Embodiment

In the first embodiment section, the embodiment was described in which both temporal and pile-up corrections are performed only for the detector of the reference detection unit 350. However, there may arise a need to perform temporal corrections for the entire part of photon counting scheme based X-ray detector to detect X-rays. Hence, an embodiment in which both temporal and pile-up corrections are also performed for the X-ray detector 320 is described. Because this embodiment differs from the first embodiment only in terms of a way of correction, changes from the first embodiment only reside in the "flow of imaging process" section. So, the changes in the "flow of imaging process" are set forth below.

[Flow of Imaging Process]

Figure 12:
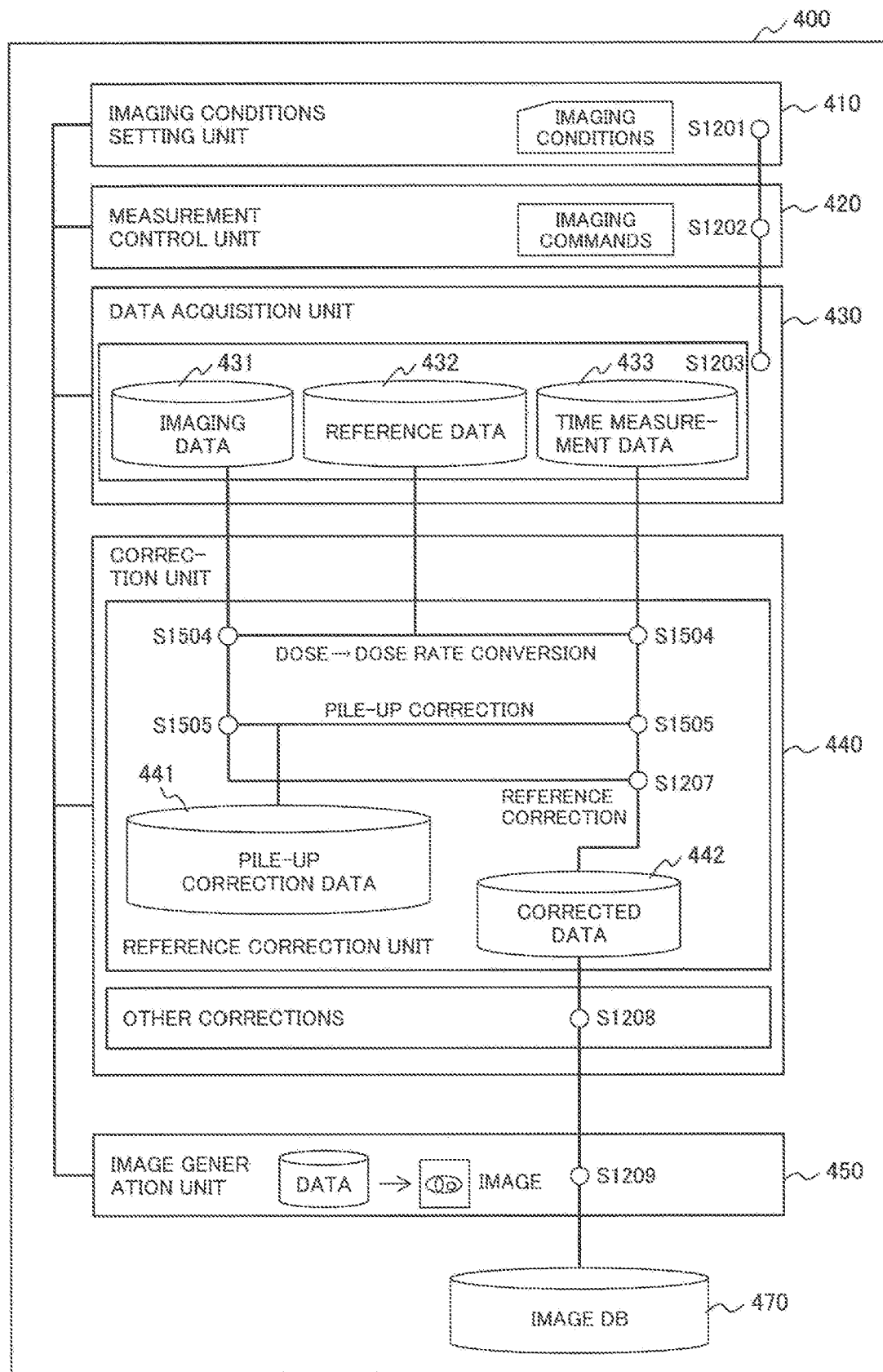
FIG. 12 is a diagram illustrating, by way of example, functional blocks of the computation section and a processing flow pertaining to the third embodiment.

The flow of imaging process, changed from the first embodiment, according to the present embodiment is depicted in FIG. 12. Now, pile-up correction data 441 is assumed to have been created beforehand in the same way as in the "flow of preprocessing for imaging" for the first embodiment.

First, the imaging conditions setting unit 410 accepts imaging conditions from the user via the UI section 200 (step S1201). Then, the measurement control unit 420 executes measurements (S1202) according to the imaging conditions set at step S1201 and the data acquisition unit 430 acquires various sets of data (step S1203). Because there is no change from the first embodiment up to this point, details are omitted.

After that, the correction unit 440 corrects the imaging data 431 and reference data 432 acquired by the data acquisition unit 430. With respect to each energy range in each of the above data, the correction unit executes a conversion of dose→dose rate, which converts a dose per view to a dose per unit time, or a dose rate (step S1504). This is because pile-up depends on a dose rate, but not a dose and a dose per view is not equivalent to a dose rate, since time for a view fluctuates or varies among views, as noted for the first embodiment. As for a way of the conversion, a conversion to a dose rate is made for each view through the use of time per view based on the time measurement data 433 with respect to both the imaging data 431 and the reference data 432 in the present embodiment.

Then, the correction unit executes a pile-up correction, using both the imaging data and reference data converted to a dose per unit time, or a dose rate (step S1505). As for a way of the pile-up correction, execute corrections of counts for each energy range with respect to both the imaging data and reference data converted to a dose rate, using pile-up correction data 441 created in the flow of preprocessing for imaging. Both the data corrected here is data per unit time.

Hence, a conversion of dose rate→dose (step S1206) executed in the first embodiment is not required to be done.

After this units matching, the correction unit executes a reference correction with respect to the imaging data (step S1207). Subsequent processing is the same as in the first embodiment.

According to the PCCT apparatus of the present embodiment, with regard to both imaging data and reference data, it is possible to measure temporal fluctuations in the rotational direction more accurately and correct fluctuations pertaining to the X-ray source, while correcting deviations per energy range attributed to detector characteristics, which occur in the reference detection unit, especially through steps S1504 and S1505; therefore, corrections can be performed with high accuracy.

Fourth Embodiment

The present embodiment is an embodiment of the PCCT apparatus configured such that pile-up can be reduced more in comparison with the structure of the first embodiment. To reduce the amount of pile-up, the intensity of incident X-rays received by the detector should be reduced. Therefore, the apparatus of the present embodiment is adapted to reduce the amount of pile-up for the reference detection unit 350 by making the size, or X-ray detection area of the X-ray detector of the reference detection unit 350 smaller than the size, or X-ray detection area of the X-ray detector 321 of the X-ray detection unit 320. Alternatively, the reference detection unit 350 is configured of a plurality of X-ray detectors whose size is equal to or smaller than the size of the X-ray detector 321. By switching between or among the X detector sizes of the reference detection unit 350 depending on the X-ray dose, a more accurate reference correction can be performed.

Figure 7A:
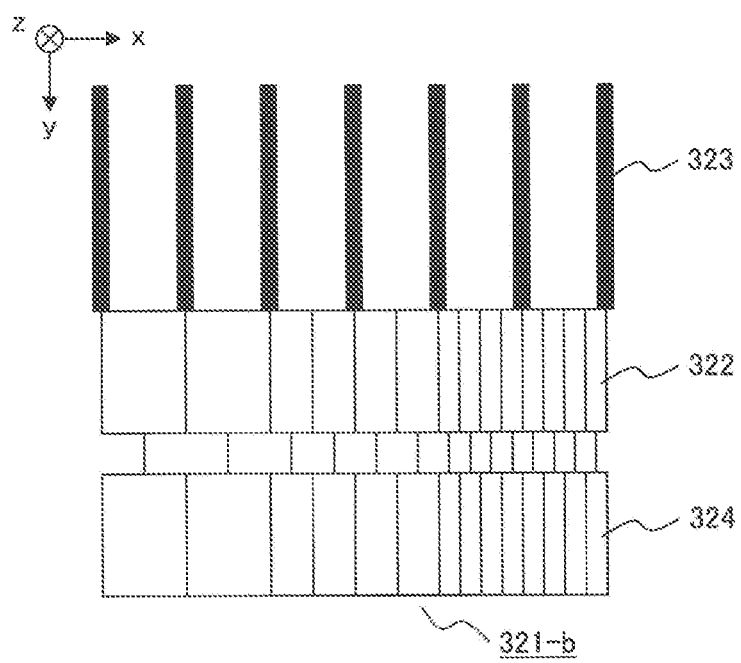
FIGS. 7A and 7B are diagrams illustrating one example of the X-ray detector pertaining to the fourth embodiment.
Figure 7B:
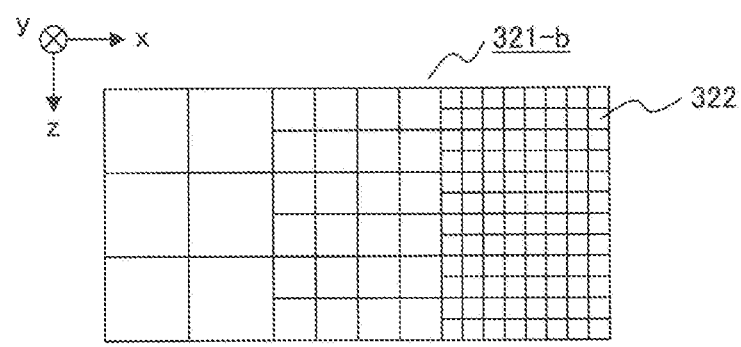

As depicted in a cross-sectional structure and a planar structure in FIGS. 7(a) and (b), an X-ray detector 321-b having a plurality of sizes, i.e., detection regions with a plurality of sizes is used in the reference detection unit 350 in the present embodiment. Using the elements with a plurality of sizes is because doses vary depending on, inter alia, the size of the object 101 and a portion to be imaged. For instance, a detector having a large detection region is used under an imaging condition of a very low dose and a small-size X-ray detector is used under an imaging condition of a very high dose.

Figure 8A:
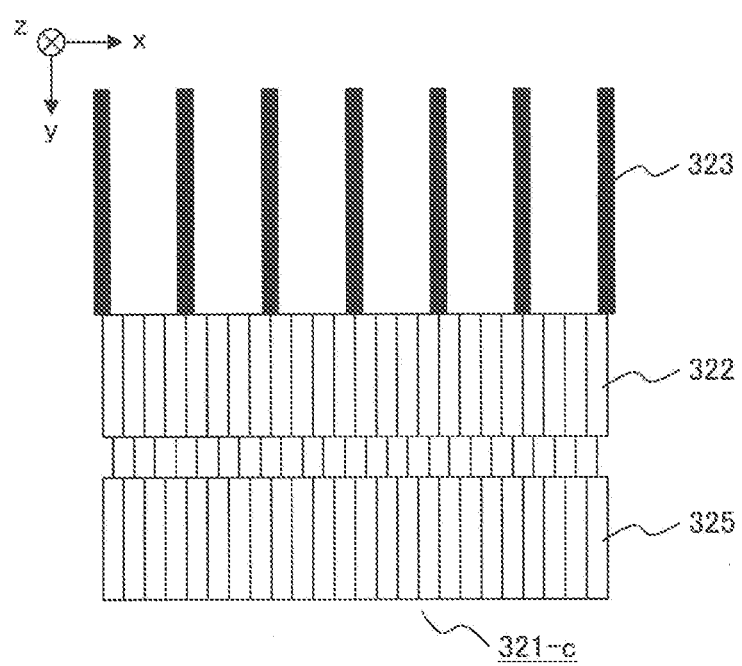
FIGS. 8A and 8B are diagrams illustrating another example of the X-ray detector pertaining to the fourth embodiment.
Figure 8B:
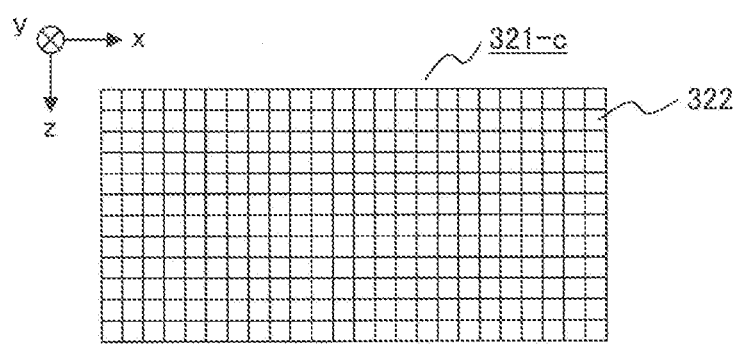

In addition, as depicted in a cross-sectional structure and a planar structure in FIGS. 8(a) and (b), only a detector 321-c of the smallest size is produced. Because a detection signal equivalent to that detected by a large detector can be acquired by adding a plurality of detection signals detected by the detector 321-c, it may be possible to eliminate the use of a large size detector.

Figure 9:
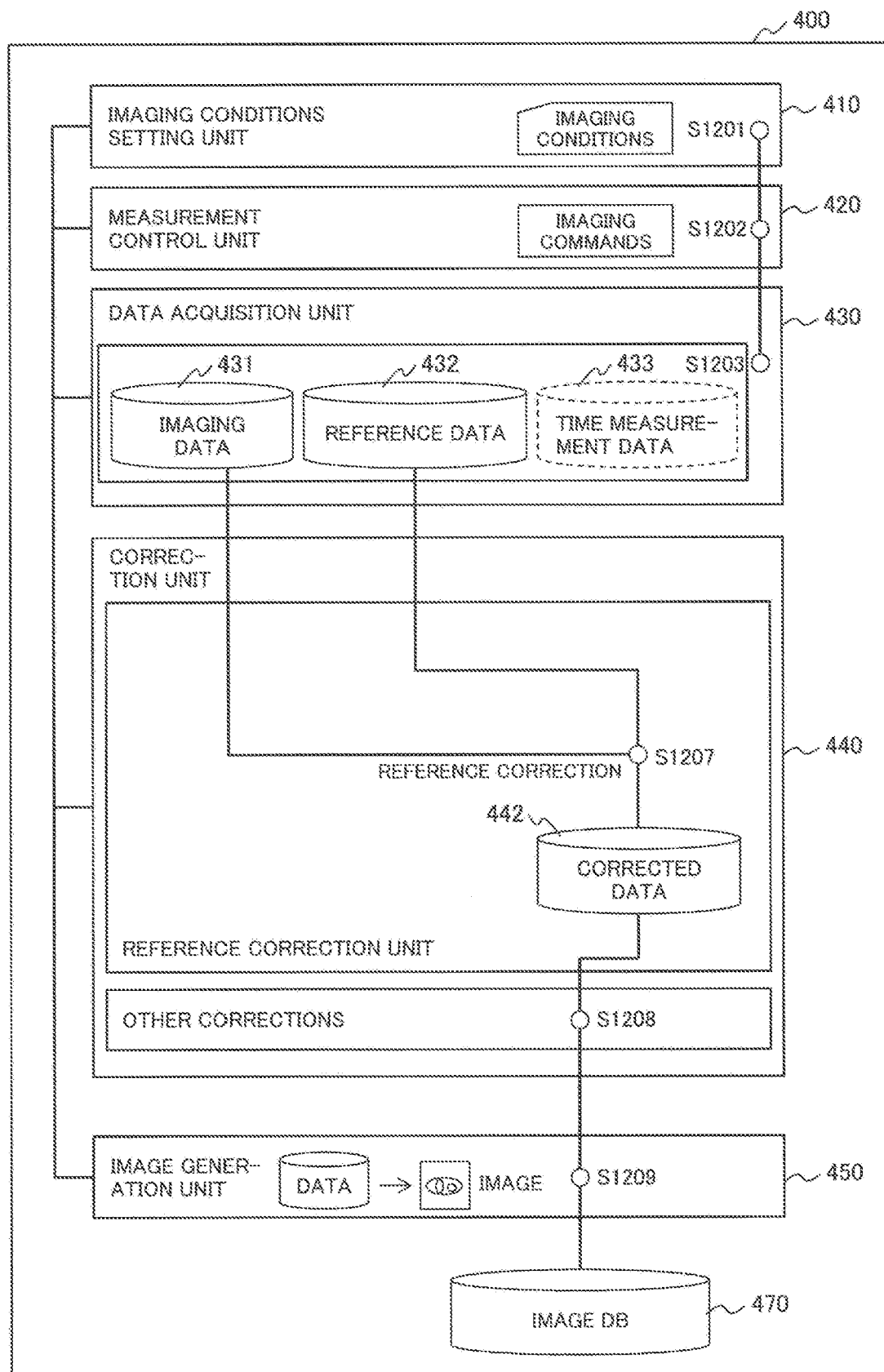
FIG. 9 is a diagram illustrating, by way of example, functional blocks of the computation section of the PCCT apparatus and a processing flow pertaining to the fourth embodiment.

Owing to the above structure, the reference detection unit 350 is less affected by pile-up and, consequently, the chart of the "flow of imaging process" within the correction unit 440 differs. As depicted in FIG. 9, in the present embodiment, corrections are performed by a procedure dispensing with steps S1204 to S1206, i.e., a pile-up correction for the reference detection unit 350, as compared with FIG. 3. Other steps and their description are the same as in FIG. 3. Also, in the present embodiment, it is not required to acquire pile-up correction data 441 acquired in the [flow of preprocessing for imaging]. Hence, time measurement data 433 measured by the time measuring instrument 345 is not needed, but the time measurement data 433 may be used for a pile-up correction or other corrections for the X-ray detector 321.

According to the present embodiment, in both cases where a detector whose elements have a plurality of sizes is used in the reference detection unit 350 and where only a detector of the smallest size is produced, it would become possible to reduce pile-up and perform a reference correction more accurately. Moreover, in the case where a detector whose elements have a plurality of sizes is used, the number of circuits for processing detection signals can be reduced in comparison with the case where only a detector of the smallest size is produced.

Fifth Embodiment

A filter capable of varying X-ray amount to vary the amount of incident X-rays received by the reference detection unit is used in a fifth embodiment, whereas the size of detector elements in the reference detection unit is varied in the fourth embodiment. That is, this embodiment is configured such that the apparatus is further equipped with a filter capable of varying X-ray amount, adapted such that filter switching can be made depending on the X-ray amount delivered by the X-ray irradiation unit, the filter being located between the reference detection unit and the X-ray irradiation unit. Changes from the foregoing embodiments reside in [gantry], [flow of preprocessing for imaging], and [flow of imaging process].

[Gantry]

Figure 10:
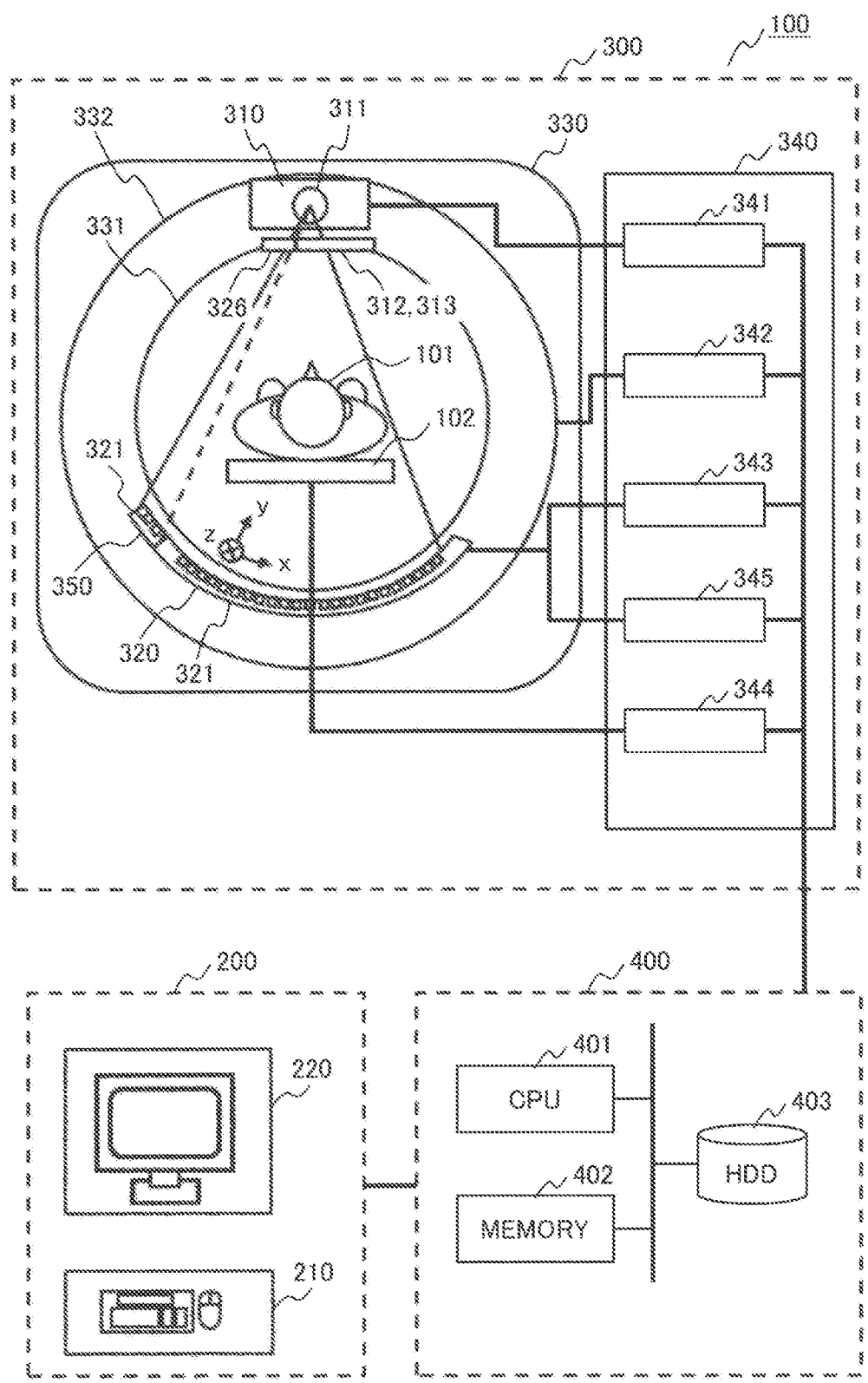
FIG. 10 is a diagram depicting one example of a structure of the PCCT apparatus pertaining to a fifth embodiment.

In the present embodiment, a filter 326 capable of varying X-ray amount is provided between the reference detection unit 350 and the X-ray irradiation unit 310, as depicted in FIG. 10. The filter 326 capable of varying X-ray amount has a mechanism enabling insertion and removal of, for example, a plurality of metal plates and the type of the metal plates is, for example, copper among others. By inserting these metal plates, it is possible to reduce the amount of incident X-rays received by the reference detection unit 350 and reduce the pile-up amount. On the other hand, when the metal plates are inserted, signal amounts per energy range change. Hence, it is required to measure beforehand proportions of signal amounts among energy ranges when the filter is inserted.

Now, the thickness of the metal plates of the filter 326 capable of varying X-ray amount depends on the amount of tube current set as specified by the user as one of imaging conditions; hence, the filter 326 capable of varying X-ray amount need not operate in conjunction with the X-ray filter 312. For this reason, another dive mechanism is provided separately from that for the X-ray filter 312 and the bowtie filter 313. However, the filter 326 capable of varying X-ray amount is only required to be independent of the X-ray filter 312 and the bowtie filter 313; the filter 326 capable of varying X-ray amount may be placed between the X-ray filter 312 as well as the bowtie filter 313 and the reference detection unit 350 and, also, it is possible to place the filter 326 capable of varying X-ray amount in a position far from the X-ray tube, such as a position right in front of the reference detection unit 350.

[Flow of Preprocessing for Imaging]

When the filter 326 capable of varying X-ray amount is used, the X-ray attenuation rate varies with respect to each energy range because of the filter. Therefore, it is required to obtain beforehand X-ray amounts per energy range with and without the filter and prepare correction data. A measurement method for such correction data is set forth below.

First, set the X-ray tube 311 to one of settable doses. In addition, remove both the bowtie filter 313 and the X-ray filter 312. Carry out X-ray irradiation in this condition. At the reference detection unit 350, measure signals in both a state where the filter 326 capable of varying X-ray amount is placed and a state where the filter is not placed. With the metal plates inserted, signals detected at the reference detection unit 350 need not be corrected because pile-up is reduced. However, with the metal plates not inserted, pile-up occurs and, therefore, executes a pile-up correction for each energy range. Then, acquire proportions of signals detected with and without the metal plates as correction data. This correction data should be prepared as correction data for the filter capable of varying X-ray amount; measure correction data for the filter capable of varying X-ray amount with respect to all settable doses.

How to create correction data concretely is set forth. First, measure incident signal amounts per energy bin received by the X-ray detection unit 320 when the filter 326 capable of varying X-ray amount is not inserted, as normal measurements. For instance, it is assumed that the measurements are 100 counts for bin1, 1000 counts for bin2, 1000 counts for bin3, and 700 counts for bin4. Then, measure signal amounts when the filter 326 capable of varying X-ray amount is inserted as per conditions specified by the user; for instance, it is assumed that the measurements are 90 counts for bin1, 850 counts for bin2, 600 counts for bin1, and 200 counts for bin4. Measure such data according to all settable conditions.

[Flow of Imaging Process]

Figure 11:
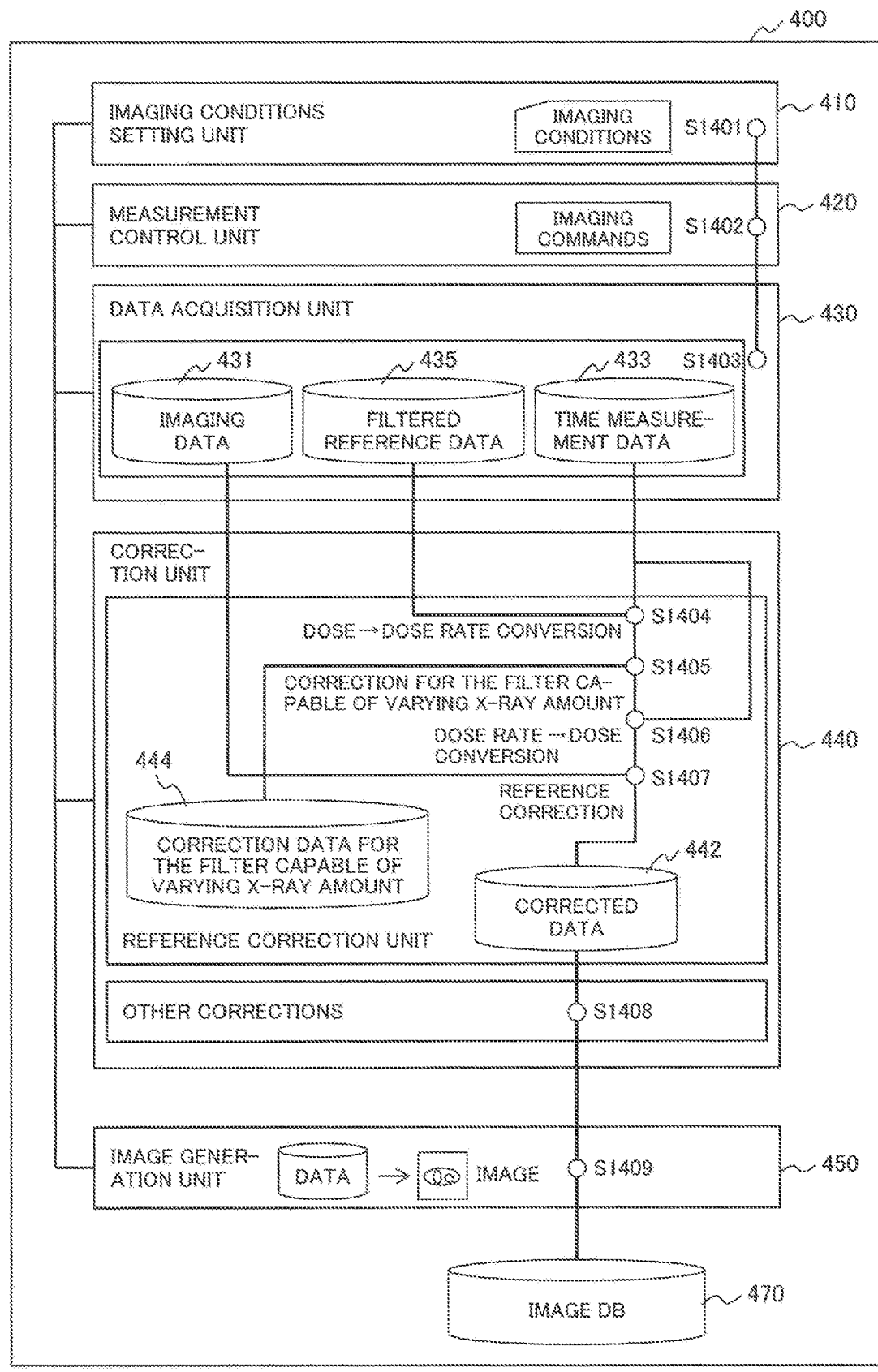
FIG. 11 is a diagram illustrating, by way of example, functional blocks of the computation section and a processing flow pertaining to the fifth embodiment.

A flow of an imaging process to be performed by the computation section 400 according to the present embodiment is described. FIG. 11 is a processing flow of the imaging process according to the present embodiment. Correction data 444 for the filter capable of varying X-ray amount is assumed to have been create beforehand in the [flow of preprocessing for imaging], as described previously.

Step S1401 to be executed by the imaging conditions setting unit 410 and step S1402 to be executed by the measurement control unit 420 are the same as step S1201 and step S1202 respectively. The data acquisition unit 430 acquires various sets of data (step S1403). In the data acquisition unit 430, by acquiring such data, imaging data 431 acquired through the X-ray detection unit 320, which includes information on the object 101, and time measurement data 433 acquired through the time measuring instrument 345 are the same as in the previous embodiment. However, reference data acquired through the reference detection unit 350 involves different amounts of attenuation per energy range attributed to the filter 326 capable of varying X-ray amount. Here, acquired reference data is referred to as filtering reference data 435.

After that, the correction unit 440 corrects the imaging data 431 acquired by the data acquisition unit 430. First, for the filtering reference data 435, the correction unit executes a conversion of dose→dose rate, which converts a dose per view to a dose per unit time, or a dose rate with respect to each energy range (step S1404). The reason for this is the same as noted for the foregoing embodiments. Then, using the data converted to dose per unit time, the correction unit executes a correction for the filter capable of varying X-ray amount (step S1405). As for a way of the correction for the filter capable of varying X-ray amount, correct count values per energy range acquired through the reference detection unit 350, using correction data 444 for the filter capable of varying X-ray amount created in the [flow of preprocessing for imaging]. As a way of the correction, perform a division according to signal amounts per bin measured using the filter 326 capable of varying X-ray amount under the same condition as set previously. Now, based on a criterion conversion value, a division by a ratio to that value may be performed.

As is the case for the foregoing embodiments, because output data at step S1405 is data per unit time, the correction unit executes a conversion of dose rate -> dose (step S1406), which is a reverse operation to step S1404. Now, as is the case for the foregoing embodiments, without making the conversion to a dose at step S1406, matching the units of corrected data with the units of imaging data may be effected by executing the same conversion to dose rate as done at step S1404 with respect to the imaging data 431.

Finally, the correction unit executes a reference correction (step S1407). Based on correction data created at steps 1404 to 1406, the correction unit corrects fluctuations in the X-ray counts, thus obtaining corrected data 442.

Subsequently, as is the case for the foregoing embodiments, the correction unit executes other corrections (step S1408) and the image generation unit 450 generates an image using corrected data and stores the image into the image DB 470 (step S1409); then the process finishes.

If corrections with respect to imaging data 431, as set forth in the third embodiment, have to be performed in the present embodiment as well, perform the S1404 and S1405 processing steps with respect to the imaging data 431 as well. Because both outputs obtained at S1405 are consistent data per unit time, skip the operation at S1406 and a reference correction at S1407 should be executed.

In the present embodiment, a pile-up correction for the reference detection unit is not required to be done, owing to, especially, steps s1404 to S1407; therefore, data processing can be performed at a higher speed.

The present invention is not limited to the described embodiments and various modifications are included therein. For example, the foregoing embodiments are those described in detail for better understanding of the present invention and the invention is not necessarily limited to those including all components described. A subset of the components of an embodiment can be replaced by components of another embodiment. To the components of an embodiment, components of another embodiment can be added. For a subset of the components of each embodiment, other components can be added to the subset or the subset can be removed or replaced by other components.

Furthermore, the described embodiments presuppose creating a program implementing some or all of the aforementioned components, functions, processing units, etc. Needless to say, some or all of them may be implemented by hardware; for example, by designing an integrated circuit, such as ASIC (Application Specific Integrated Circuit) or FPGA (Field Programmable Gate Array), to implement them.

REFERENCE SIGNS LIST

100 . . . PCCT apparatus
101 . . . Object
102 . . . Table
200 . . . UI section
210 . . . Input device
220 . . . Output device
300 . . . Measurement section
310 . . . X-ray irradiation unit
311 . . . X-ray tube
312 . . . X-ray filter
313 . . . Bowtie filter
320 . . . X-ray detection unit
321 . . . X-ray detector
322 . . . Detection element
323 . . . Collimator 324 . . . Counting circuit
325 . . . Integration circuit
326 . . . Filter capable of varying X-ray amount
330 . . . Gantry
331 . . . Bore
332 . . . Rotary plate
333 . . . Notch
340 . . . Control unit
341 . . . Irradiation controller
342 . . . Gantry controller
343 . . . Detection controller
344 . . . Table controller
345 . . . Time measuring instrument
350 . . . Reference detection unit
400 . . . Computation section
401 . . . Central processing unit
402 . . . Memory
403 . . . HDD device
410 . . . Imaging conditions setting unit
420 . . . Measurement control unit
430 . . . Data acquisition unit
431 . . . Imaging data
432 . . . Reference data
433 . . . Time measurement data
434 . . . Integrated reference data
435 . . . Filtering reference data
440 . . . Correction unit
441 . . . Pile-up correction data
442 . . . Corrected data
443 . . . Integration→energy range conversion data
444 . . . Correction data for the filter capable of varying X-ray amount
450 . . . Image generation unit
470 . . . Image database (DB)

The invention claimed is:

1. A photon-counting CT apparatus comprising:
   an X-ray irradiation unit which delivers X-rays;
   a photon counting scheme based X-ray detection unit which detects the X-rays;
   a data acquisition unit which counts X-ray photons detected by the X-ray detection unit for each of energy ranges which are predetermined divisions of energy, thus acquiring measurement information for each of the energy ranges;
   a reference detection unit which measures fluctuations in X-rays delivered from the X-ray irradiation unit;
   a time measuring unit which measures temporal fluctuations in a rotational direction of the X-ray irradiation unit; and
   a correction unit which corrects measurement data measured by the reference detection unit, based on time measurement data measured by the time measuring unit.

2. The photon-counting CT apparatus according to claim 1,
   wherein the correction unit corrects the measurement information measured by the data acquisition unit, based on the time measurement data.

3. The photon-counting CT apparatus according to claim 1,
   wherein the correction unit converts measurement data acquired through the reference detection unit to dose rate data using the time measurement data.

4. The photon-counting CT apparatus according to claim 3,
   wherein the correction unit corrects the dose rate data, based on pile-up correction data obtained by measuring beforehand the dose rate data and the amount of change in the measurement information attributed to pile-up.

5. The photon-counting CT apparatus according to claim 4,
   wherein the correction unit converts the corrected dose rate data to dose data using the time measurement data.

6. The photon-counting CT apparatus according to claim 5, wherein the correction unit corrects measurement information for each of the energy ranges, based on the dose data resulting from conversion.

7. The photon-counting CT apparatus according to claim 1,
   wherein a size of an X-ray detector of the reference detection unit is smaller than a size of an X-ray detector of the X-ray detection unit.

8. The photon-counting CT apparatus according to claim 1,
   wherein the reference detection unit is configured of a plurality of X-ray detectors whose size is equal to or smaller than the size of the X-ray detector of the X-ray detection unit.

9. The photon-counting CT apparatus according to claim 1, comprising a filter capable of varying X-ray amount, adapted such that X-ray filter changing can be made depending on the X-ray amount delivered by the X-ray irradiation unit, the filter being located between the reference detection unit and the X-ray irradiation unit.

10. The photon-counting CT apparatus according to claim 1,
    wherein the reference detection unit is configured as an integration type detector; and
    based on a relation, obtained beforehand with regard to X-rays delivered from the X-ray irradiation unit, between signal amounts detected by the reference detection unit and measurement information for each of the energy ranges obtained through the X-ray detection unit, the correction unit makes corrections of the measurement information per energy range from a relation with measurement information for each of the energy ranges obtained through the X-ray detection unit when imaging an object is performed and a relation with signal amounts detected by the reference detection unit during imaging.

11. The photon-counting CT apparatus according to claim 1,
    wherein a size of an X-ray detector of the reference detection unit is smaller than a size of an X-ray detector of the X-ray detection unit.

12. The photon-counting CT apparatus according to claim 1,
    wherein the reference detection unit is configured of a plurality of X-ray detectors whose size is equal to or smaller than the size of the X-ray detector of the X-ray detection unit.

13. The photon-counting CT apparatus according to claim 1, further comprising a filter capable of varying X-ray amount, adapted such that X-ray filter changing can be made depending on the X-ray amount delivered by the X-ray irradiation unit, the filter being located between the reference detection unit and the X-ray irradiation unit.

14. The photon-counting CT apparatus according to claim 2, further comprising a filter capable of varying X-ray amount, adapted such that X-ray filter changing can be made depending on the X-ray amount delivered by the X-ray irradiation unit, the filter being located between the reference detection unit and the X-ray irradiation unit.

\* \* \* \* \*